United States Patent [19]

Juntti

[11] Patent Number: 4,527,750
[45] Date of Patent: Jul. 9, 1985

[54] APPARATUS FOR CUTTING OUT STRIPS FROM FLEXIBLE WEBS

[76] Inventor: Lars Juntti, Poppovägen 19, S-82500 Iggesund, Sweden

[21] Appl. No.: 511,168
[22] PCT Filed: Oct. 7, 1982
[86] PCT No.: PCT/SE82/00320
 § 371 Date: Jun. 9, 1983
 § 102(e) Date: Jun. 9, 1983
[87] PCT Pub. No.: WO83/01507
 PCT Pub. Date: Apr. 28, 1983

[30] Foreign Application Priority Data

Oct. 13, 1981 [SE] Sweden .................... 8106046

[51] Int. Cl.³ .................... B65H 35/02; B26D 5/20
[52] U.S. Cl. .................... 242/56 R; 242/56.4; 83/919; 83/614
[58] Field of Search .................... 242/56 B, 56 R, 56.4; 83/919, 924, 614, 117, 115

[56] References Cited

U.S. PATENT DOCUMENTS

| | | | |
|---|---|---|---|
| 2,519,159 | 8/1950 | Talbot | 83/919 X |
| 2,837,155 | 6/1958 | Cundiff et al. | 83/919 X |
| 3,668,922 | 6/1972 | Fleming et al. | |
| 4,022,095 | 5/1977 | Jones | 83/614 X |

FOREIGN PATENT DOCUMENTS

1067616 10/1959 Fed. Rep. of Germany .
 346618 7/1972 Sweden .

Primary Examiner—Stanley N. Gilreath
Assistant Examiner—Leo J. Peters
Attorney, Agent, or Firm—Spencer & Frank

[57] ABSTRACT

An apparatus for cutting out strips from a web wound to the shape of a cylindrical roll, includes a carrier, at least two spaced-apart cutting members mounted on the carrier for cutting out the strips between each other, a rotatable core for winding up a web strip cut out by the cutting members, contact members mounted on the carrier for exerting a pressure against an outermost web layer so as to firmly hold the layer in place when moving the apparatus axially along the cylindrical surface of the roll, and a resilient mechanism for providing a relative resilient mobility between the cutting members and the contact members toward or away from the outermost web layer, so as to permit the application of the apparatus against the cylindrical surface of rolls irrespective of varying diameters thereof.

8 Claims, 5 Drawing Figures

APPARATUS FOR CUTTING OUT STRIPS FROM FLEXIBLE WEBS

THE BACKGROUND OF THE INVENTION

In conventional paper making machines paper is produced in the form of a continuous web, which—after having passed the driver section and any platers of the machine—is wound up onto the so called jumbo reel. This consists of a heavy steel cylinder which is capable of carrying wound paper webs having a length of ten thoudsands of meters and a width of about 3 to 10 meters. When the winding of the web onto the jumbo reel has been finished it is necessary to select therefrom a number of test samples in order to make it possible to lay down the quality as well as other properties of the paper produced. Simple tests may be made by the machine operator himself, while more complicated tests have to be accomplished in a laboratory. Irrespective of the testing technique used the selection of the necessary test samples from the wound and roll-shaped paper web, which rests motionless on the jumbo reel, has hitherto been carried out quite simply by letting two operators manually tear off or by means of a knife cut off a strip along the entire machine width (i.e. along the entire length of the wound paper roll). The strip thus torn or cut off may then either be divided into smaller pieces or in its entirety be brought into the test equipment in question. To tear or cut off a strip in the manner described is, however, connected with many disadvantages. Firstly it is a troublesome and ergonomically unfavourable work for the operators to try to extract an expedient strip, which often is very long, from a material which is flabby and cumbersome. In pratice the result usually will be that the extracted strip is more or less sharply battered; what makes the strip unsuitable for certain tests. Further the strip seldom becomes straight, but rather wry or wave-like with irregular borders. When handled in sophisticated test equipment such strips will cause problems. Finally it should be stressed that the necessity of having two operators to carry out the test sample extraction may involve extra costs.

BRIEF DISCLOSURE OF THE INVENTION

The present invention aims at facilitating the extraction of strips from paper or similar webs and making it possible to obtain undamaged and exactly straight strips which are easy to handle. This is achieved by an apparatus comprising a carrier having at least two mutually spaced-apart cutting members for cutting out at least one strip therebetween. This apparatus is characterized in that the carrier is movable along a substantially immobile web and comprises a core which is rotatable about its own axis, a web strip cut out by the cutting members being windable onto said core with a periphery speed which is substantially equal to the speed of motion of the carrier in relation to the web so as to always keep each strip neatly stretched during the winding thereof onto the core.

FURTHER ELUCIDATION OF THE PRIOR ART

By the DE patent specification No. 1067616 and the Swedish patent application No. 16832/67 (publication No. 346618) it is previously known to cut out test strips from paper webs by means of apparatuses comprising two spaced-apart cutting members mounted on a carrier. In these cases, however, the apparatus is stationary and arranged to cut out a single strip from the running paper web in a paper making machine and none of the apparatuses presents any means whatsoever for winding up the strips in such a manner that the strips do not risk to be mechanically damaged. As a matter of fact the apparatuses of the above-mentioned publications are moisture test auxiliary devices.

DETAILED DESCRIPTION OF A PREFERRED EMBODIMENT OF THE INVENTION

Figure 1:
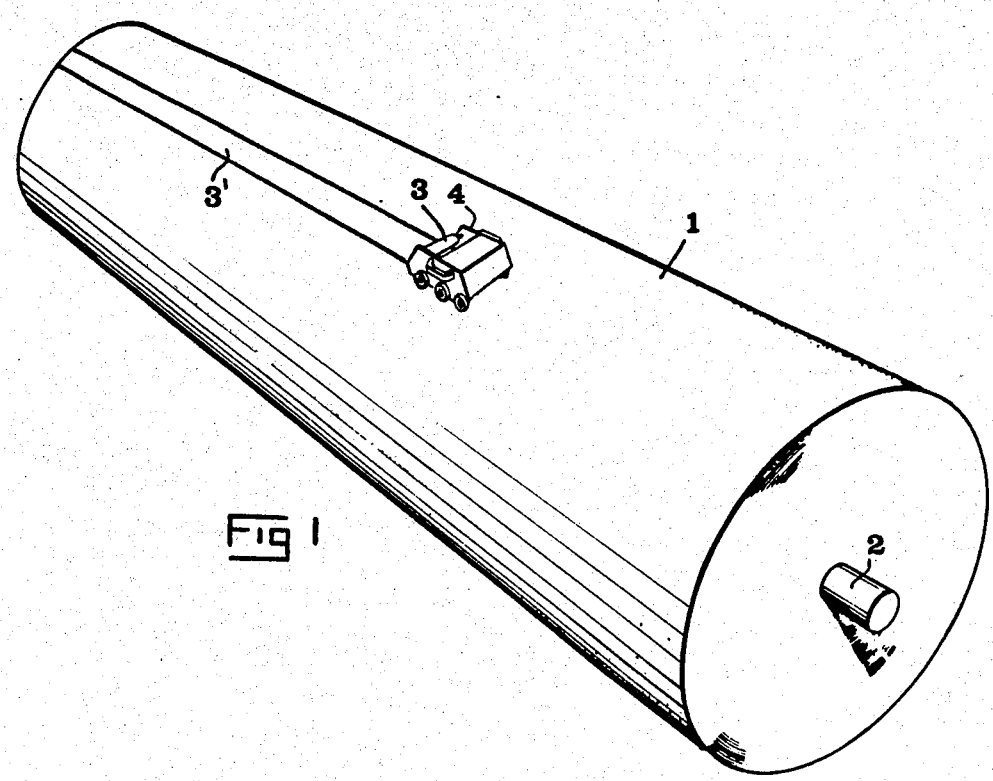
FIG. 1 is a perspective view illustrating the apparatus according to the invention when cutting out a test strip from a paper roll.
Figure 2:
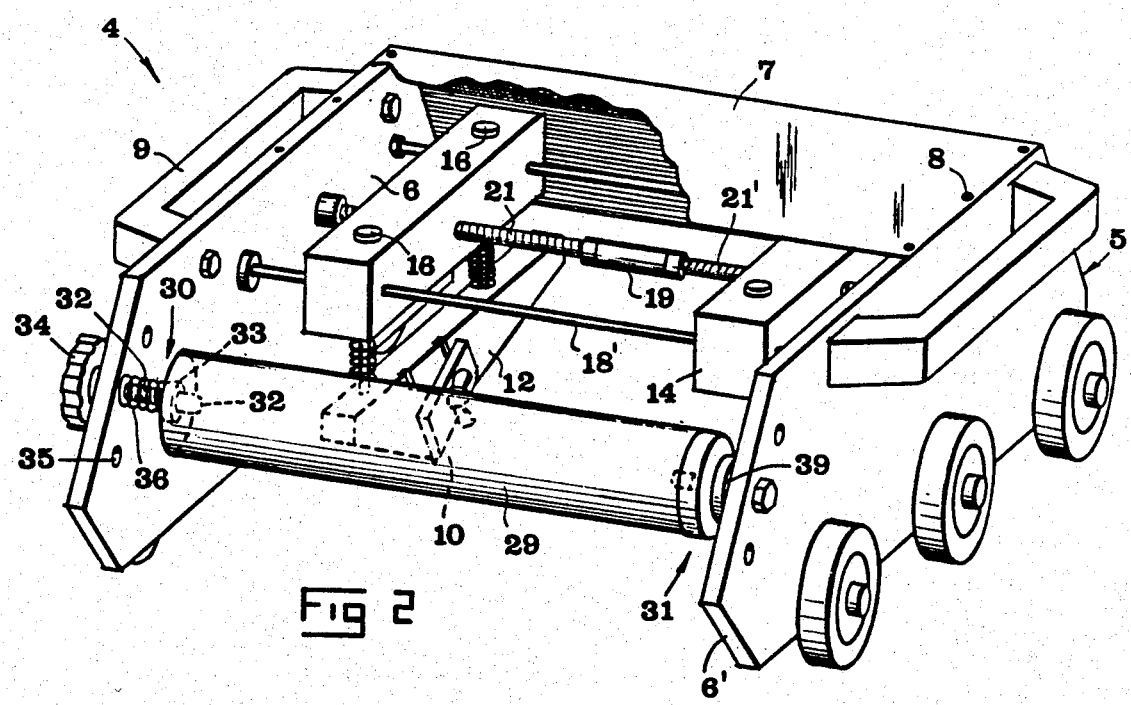
FIG. 2 is a perspective view of the apparatus looked at obliquely from above, portions of the apparatus having been cut away for the purpose of clarification.

FIG. 1 illustrates a paper web 1 which in the usual way is wound onto a jumbo reel 2. The paper in question may consist of newsprint paper, fine paper, cardboard, sack paper, etcetera. As previously mentioned the length of the web may amount to ten thousands of meters while the width may amount to about 10 meters. For cutting out a strip 3 an apparatus generally designated 4 is used, the strip cut out leaving a slit 3' in the outermost layer of the web. The apparatus 4 will be described in detail with reference to FIGS. 2 to 5.

In the embodiment shown the apparatus consists of a wheeled carriage comprising a framing 5 which is composed of two spaced-apart upright side pieces 6,6' kept together by means of a transverse piece 7 in the form of a bent plate, which is attached to the respective side pieces in any suitable manner, e.g. by means of screws 8. Onto the outside of the side pieces 6,6' handles 9 are attached by means of which the carriage may be caught hold of and manually moved along the circumferential surface of the paper roll 1.

For the purpose of cutting out the strip 3 from the paper web the carriage is provided with two spaced-apart cutting members 10,10'. In this case the element that properly performs the cutting consists of a knife blade 11 mounted on a runner-like body 12 having a sliding surface 13 intended to slide along the circumferential surface of the paper roll 1. The runner body 12 is supported by a block 14 through two supporting bars 15, which pass through holes in the block 14 and which are provided with stop washers 16 at the top thereof. Between the block 14 and the runner body 12 compression springs 17 are acting which always aim at moving the runner body downwardly from the block and against the action of which the runner body is resiliently movable towards the block when the runner body is pressed against the paper roll.

The individual block 14 is displaceable along two guide rods 18,18' extending between the two side pieces 6,6'. A long screw element 19 also extends between the side pieces, said element being rotatably mounted in relation to the side pieces and having at one of its ends a control knob 20 located externally of one of the side pieces. The screw element 19 has a left-hand thread 21 for one of the blocks as well as a right-hand thread 21' for the other block. Hence it follows that both of the blocks will be moved outwardly from the centre of the apparatus when the screw element is rotated in one direction and inwardly when the screw element is rotated in the opposite direction. Advantageously the threads consist of trapezoid threads which by friction quarantee that the blocks distinctly remain in their given positions after finishing the rotation of the screw element.

The knife blade 11 previously mentioned is hold in relation to the runner body 12 by means of a clamp 22 which is movable along guiding slots 23 in the runner body and which may be clamped against said body by means of a winged screw 24 passing through an oblong aperture 25 in the body, the longitudinal axis of said aperture being parallel with the guiding slots 23. When the screw is tightened the knife blade 11, which preferrably is extremely thin, will be clamped between the clamp 22 and the body 12, the bottom tip of the blade being located at an adjustable level or depth beneath the sliding surface 13. This depth is adjusted in dependence of the thickness of the paper web in question on one hand, and on the other hand the number of paper layers that should be cut out.

It should be noted that the knife blade 11 is placed on the inside of the runner body 12. Hereby it is guaranteed that the cutting depth of blade 11 will remain constant irrespective of the diameter of the paper roll 1. If the diameters vary between different paper rolls the only thing happening will be that the runner bodies 12 move in relation to the blocks 14, the sliding surfaces 13 always being pressed against the circumferential surface of the paper roll.

Figure 3:
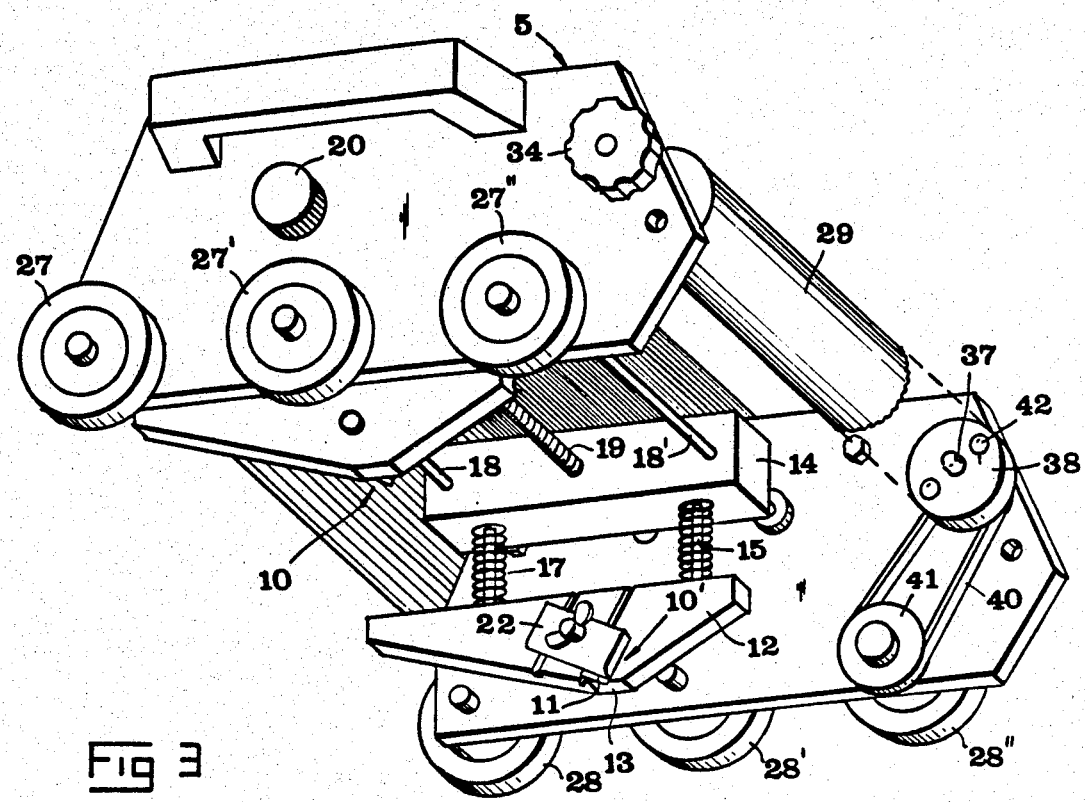
FIG. 3 is a perspective view of the apparatus looked at obliquely from below.
Figure 4:
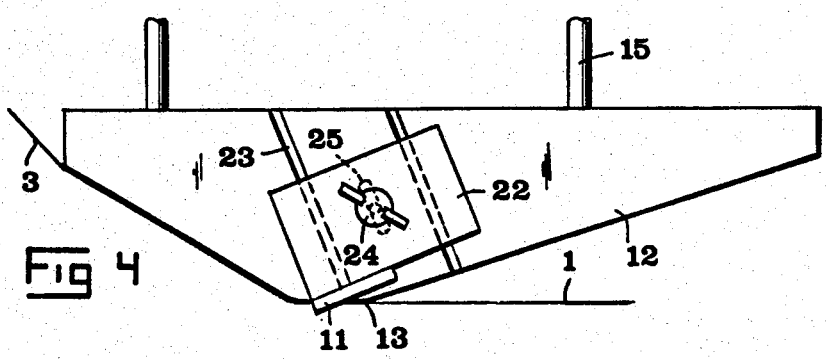
FIG. 4 is an enlarged lateral view showing a cutting member included in the apparatus.
Figure 5:
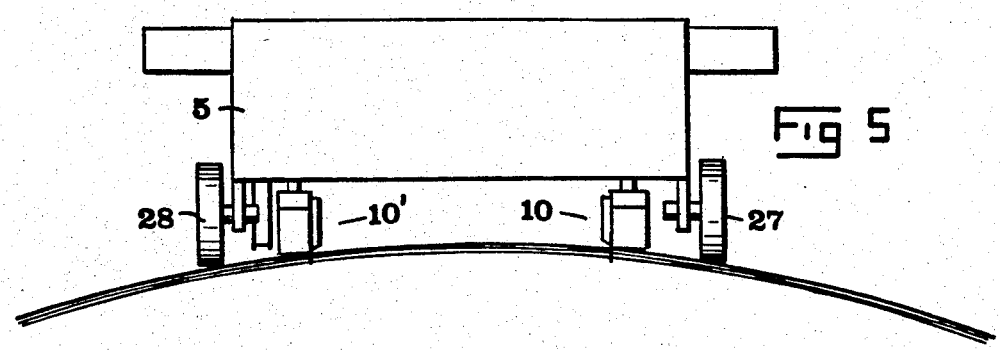
FIG. 5 is an end view of the apparatus.

FIG. 3 illustrates the fact that the carriage includes two sets of wheels, each comprising three wheels 27,27',27" and 28,28', 28" respectively, which are aligned with each other. By using three or more aligned wheels in each set of wheels in the manner shown in FIG. 3 an extremely good steering ability of the carriage is achieved so that the carriage will more or less automatically always aim at following a straight line along the circumferential surface of the paper roll.

A roller-shaped core 29 also extends between the side pieces 6,6'. On this core the paper strip 3 cut out by the knife blades 11 may be gradually wound up as the carriage is moved along the roll 1. The core 29 is dismountably arranged on the carriage so as to permit the core and the strip to be removed as one single unit from the carriage after the cutting and winding of the strip have been finished. The possibility of dismounting the core is in this case realized by connecting the two opposite ends of the core to the other parts of the carriage through first and second male-female connections 30,31. The first male-female connection 30 includes a male element 32 engaging a corresponding centrally located female recess in the gable of the core. The male element 32 consists of a tap having a stop collar 33 and a grip knob 34 outside the side piece 6. The tap 32 (to which the stop collar 33 suitably is connected by a thread connection) is simply journalled in an aperture included in a series of different apertures 35 made in the side piece 6. Between the stop collar 33 and the side piece 6 there is a compression spring 36 against the action of which the tap is movable outwardly from the centre of the carriage. Also the second male-female connection 31 comprises a central tap 37 which engages a female recess in the core 29, said recess likewise being centrally located. The tap 37 is part of a pulley 38 having a shaft (not shown) which also has a wheel or belt disk 39 included in a belt transmission 40 having a second belt disk 41 which is driven by the carriage wheel 28". On the inner surface of the pulley 38 a number of rather short, gently rounded projections 42 are provided for engagement with a number of corresponding, shallow recesses in the gable surface of the core 29. The projections 42 and the associated recesses form together a sliding clutch to which the above-mentioned compression spring 36 also belongs. The sliding clutch just described has been provided for the following reasons: The belt disk 41 associated with the carriage wheel 28" has a greater diameter than the driven belt disk 39 in order to give the transmission such a transmission ratio that the circumferential surface of the core 29 will be driven at higher periphery speed than the carriage wheels, leading to the advantage that the strip being wound up onto the core 29 will be kept neatly streched during the winding operation. The purpose of the sliding clutch between the pulley 38 and the core 29 is to reduce the overtensions occuring in the strip as a consequence of said transmission ratio.

THE FUNCTION OF THE APPARATUS

The apparatus described above operates in the following way. Depending on the thickness on the paper web in question as well as on the number of strip layers that are desired to be wound onto the core 29, the knife blades 11 are adjusted to a suitable depth in relation to the sliding surface 13 on the runner bodies 12, e.g. 0.5 to 1.0 millimeters beneath said sliding surfaces. Further the strip width desired is settled by moving the blocks 14 and thereby also the knife blades 11 to positions at a suitable distance from each other. This is done by actuating the knob 20. Here it should be noted that the rotation of the knob 20 and the associated screw element 19 will guarantee a uniform displacement of the blocks, though in opposite directions thanks to the arrangement of left-hand thread 21 and right-hand thread 21". After this the apparatus is applied against the paper roll 1 shown in FIG. 1, more precisely at an end thereof. When the two knife blades 11 have started to cut out the strip 3, the end thereof is attached to the core 29. In practice this may be carried out in many different ways. Thus a thin slot (not shown) may be recessed in the core, the strip end being put into said slot. The strip end may also be hooked onto a number of needles projecting from the circumferential surface of the core. It is further possible to attach the strip end by means of a suitable adhesive on the core. When the strip end is secured to the core the carriage is moved axially along the circumferential surface of the paper roll 1 from one end thereof to the other. During this movement at least one strip having exactly parallel borders is continuously cut out from the web, the strip being automatically wound up onto the core due to the rotation of the wheel 28". Thereby the strip will be in an undamaged condition suited for the purpose of testing the same. In this connection it should be stressed that the wheels exert a certain pressure against the outermost layer of the paper web. This pressure guarantees that the outermost web layer or layers are firmly held in place and streched at the same time as the knife blades penetrate the same. Accordingly there will be no tendenly of the paper to crumple when cut by the knife blades. By the resilient contact of the runner bodies 12 against the circumferential surface of the paper roll a uniform cutting depth is achieved along the entire length of the roll irrespective of the diameter of the roll, since the sliding surfaces of the runner bodies will always contact the surface of the paper roll with a suitable spring pressure. When the cutting of the strip has been finished the strip may be removed from the carriage together with the core and be delivered to the testing station in question. This is simply made by pulling out the gripping knob 34 some distance from the side piece 6 so as to release the male element 32 from the engagement with the associated recess in the core. The core accordingly released may then immediately be replaced by another core taken from a supply laid up for this purpose.

CONCEIVABLE MODIFICATIONS OF THE INVENTION

Of course the invention is not merely limited to the embodiment described above and shown in the drawings. Thus it is possible to use—instead of a wheeled carriage—other means as a carrier for the cutting members and the core, e.g. a slide having runners instead of wheels for contacting the web to be treated. The carrier in question may further be movable along guides running parallell to the material web in question. Instead of fixed knife blades as cutting members one may use rotating cutter wheels or any other means capable of making cuts confining the desired strip in the web. The number of cutting members may be greater than two so as to simultaneously cut out two or more strips located side by side. The apparatus according to the invention is not limited to the treatment of just paper either, but may be used when cutting out strips from flexible webs of any arbitrary material, such as plastics, rubber, paper pulp, etcetera. Further the apparatus may be provided with means facilitating the handling thereof. Thus indexes may be mounted on the blocks 14 for co-operation with a scale attached to the transverse plate 7, said scale disclosing the current strip width which is settled by the distance between the knife blades or cutting members. Though the preferred embodiment of the invention has been designed with resiliently movable cutting members in order to make possible an automatic adjustment of the cutting members to cylindrical, wound objects, the apparatus may also be designed for cutting quite flat webs only. Instead of driving the core 29 by means of a carriage wheel it is further possible to rotate the same by any other means, such as a motor. Finally it should be stressed that the apertures 35 serving as mountings for the core permit the mounting of cores having different diameters while securing the effect that the periphery of the cores is always located close to the bottom of the carriage irrespective of the actual diameter. This is advantageous in so far as the angle between the strip cut out and the untreated web in front of the cutting members will then remain small so as to avoid damages in the strip. Using cores having rather great diameters is advantageous and sometimes necessary, e.g. when paper pump webs or comparatively stiff paper qualities should be wound.

I claim:

1. Apparatus for cutting out strips from a web wound to the shape of a cylindrical roll, comprising a carrier, at least two spaced-apart cutting members mounted on said carrier for cutting out said strips between each other, a rotatable core for winding up a web strip cut out by said cutting members, contact members mounted on the carrier for exerting a pressure against an outermost web layer so as to firmly hold said layer in place when moving the apparatus axially along the cylindrical surface of the roll, and resilient means for providing a relative resilient mobility between said cutting members and said contact members toward or away from the outermost web layer so as to permit the application of the apparatus against said cylindrical surface of rolls irrespective of varying diameters thereof.

2. Apparatus as defined in claim 1, wherein said contact members comprise two sets of wheels spaced transversely to the direction of travel of the carriage, each of said sets including at least three wheels in alignment with each other.

3. Apparatus as defined in claim 1, wherein the roll core is automatically rotatable upon movement of the carriage along the web, by being connected to at least one driving carriage wheel by means of a transmission having a transmission ratio ensuring that a strip received on the core has a higher peripheral speed than said wheel whereby the strip cut out by the cutting members will be neatly stretched during the winding thereof onto the core, said transmission including a sliding clutch for making possible a simultaneous rotation of the wheels and the core notwithstanding said transmission ratio therebetween.

4. Apparatus as defined in claim 3, wherein one end of the core is connected to a framing of the carriage by means of a first male-female connection including a first male or female element mounted on the framing, said element being movable in relation to the framing and actuated by a spring urging said first male or female element into engagement with a corresponding second female or male element in the core and against the action of which said first and second elements may be separated, and the other end of the core is connected to a body rotated by the driving carriage wheel by means of a second male-female connection comprising a number of shallow, rounded recesses and projections in said body and said core respectively, said spring further urging said projections and recesses into engagement.

5. Apparatus as defined in claim 1, including means mounting the two cutting members for adjustable movement to different positions in relation to each other and in relation to the carrier in order to achieve varying strip widths, means being provided for ensuring a uniform movement of the cutting members to and from each other when adjusting the distance therebetween.

6. Apparatus as defined in claim 5, wherein the cutting members include knife blades mounted on runner-like bodies provided for sliding along the web and said runner bodies are supported by two blocks displaceable along guide bars by means of a rotatable screw having a left-hand thread for one of the blocks and a right-hand thread for the other block.

7. Apparatus as defined in claim 6, wherein means are provided for adjustably moving the knife blades and for fastening the knife blades at varying depths in relation to the runner bodies so as to make it possible to vary the number of web layers to be cut.

8. Apparatus as defined in claim 1, wherein said carriage includes a plurality of mounting means for the core, said mounting means being located at different height levels for accommodating cores of different diameters.

* * * * *